United States Patent
Cumberland et al.

(10) Patent No.: US 7,473,563 B2
(45) Date of Patent: Jan. 6, 2009

(54) ENVIRONMENTAL SAMPLING AND TESTING DEVICE

(75) Inventors: Brendi M. Cumberland, Pleasanton, CA (US); Maha El-Sayed, Pleasanton, CA (US); Alan J. Fujii, Newport Beach, CA (US); Scott D. Manske, Pleasanton, CA (US); Elias A. Shaheen, Pleasanton, CA (US)

(73) Assignee: The Clorox Company, Oakland, CA (US)

( * ) Notice: Subject to any disclaimer, the term of this patent is extended or adjusted under 35 U.S.C. 154(b) by 337 days.

(21) Appl. No.: 11/397,522

(22) Filed: Apr. 3, 2006

(65) Prior Publication Data

US 2007/0231923 A1    Oct. 4, 2007

(51) Int. Cl.
*G01N 33/53* (2006.01)

(52) U.S. Cl. .................. 436/514; 436/518; 436/524; 436/530; 436/541; 436/807; 435/287.1; 435/287.2; 435/287.9; 435/288.7; 435/970; 422/56; 422/59; 422/61

(58) Field of Classification Search .......... 436/514, 436/518, 524, 530, 541, 807; 435/7.1, 7.93, 435/7.94, 287.7, 287.8, 287.9, 288.7, 970; 422/56–61
See application file for complete search history.

(56) References Cited

U.S. PATENT DOCUMENTS

| | | | |
|---|---|---|---|
| 4,978,504 A | 12/1990 | Nason | |
| 5,078,968 A | 1/1992 | Nason | |
| 5,238,649 A | 8/1993 | Nason | |
| 5,266,266 A | 11/1993 | Nason | |
| 5,702,035 A | 12/1997 | Tsao | |
| 5,714,389 A | 2/1998 | Charlton et al. | |
| 5,869,003 A | 2/1999 | Nason | |
| 5,879,635 A | 3/1999 | Nason | |
| 5,989,921 A | 11/1999 | Charlton et al. | |
| 6,140,136 A * | 10/2000 | Lee | 436/518 |
| 6,248,294 B1 | 6/2001 | Nason | |
| 6,372,516 B1 * | 4/2002 | Sun | 436/518 |
| 6,485,982 B1 | 11/2002 | Charlton | |
| 6,593,142 B2 | 7/2003 | Kelly et al. | |
| 6,812,038 B1 * | 11/2004 | Mendel-Hartvig et al. | 436/514 |
| 6,875,184 B2 * | 4/2005 | Morton et al. | 600/573 |
| 7,220,597 B2 * | 5/2007 | Zin et al. | 436/518 |
| 2006/0040405 A1 | 2/2006 | Charlton et al. | |

* cited by examiner

*Primary Examiner*—Bao-Thuy L Nguyen
(74) *Attorney, Agent, or Firm*—Alok Goel; Richard Niehuser

(57) ABSTRACT

Provided is sampling and testing device for the detection of specific molds, allergens, viruses, bacteria, fungi, and other protein containing substances. Embodiments of the device include a sampling member slideably engaged with a base that contains a lateral flow strip adapted to detect specific analytes of interest. The sampling member defines a solvent reservoir that stores an elution solvent in a fluid-tight manner before the device is used to sample and test environmental surfaces. During slideable withdrawal of the sampling member from the base, the elution solvent stored in the reservoir is automatically released to a wick assembly of the sampling member. The wick assembly includes a wick adapted to receive, distribute, and retain the elution solvent. After a user samples an environmental surface for an analyte of interest with the elution solvent wetted wick, the sampling member is returned to the base where the wick contacts the lateral flow strip contained in the base. The wick transfers at least a portion of analyte and the elution solvent to the lateral flow strip for the calorimetric detection of specific allergens, viruses, bacteria, and other protein containing substances in the sample. The colorimetric results of the test are displayed through a window in the base.

15 Claims, 7 Drawing Sheets

ENVIRONMENTAL SAMPLING AND TESTING DEVICE

BACKGROUND OF THE INVENTION

1. Field of the Invention

The present invention relates generally to disposable colorimetric sampling devices, and, more specifically, to a user-friendly, simple to use, disposable colorimetric sampling device for the detection of one or more specific potentially harmful substances in an environmental or biological sample.

2. Description of the Related Art

Diagnostic assays for the determination of specific proteins in biological and environmental samples are commonly used across various industries (environmental, biotech, healthcare, food, etc). With the increased awareness of health and wellness in the home and other indoor environments and the outdoors, there is growing interest in assessing the presence or absence of potentially harmful substances and how efficacious household cleaning products are in denaturing or destroying molds, allergens viruses, bacteria, and other proteins known to cause negative human and animal health effects.

Colorimetric assays utilizing sampling devices for the detection of total proteins in biological samples are commonly used across various industries (biotech, healthcare, food, etc). Protein detection assays are available through biotechnology companies such as Pierce, Bio-Rad, and Biotrace International.

One such detection assay, described in U.S. Pat. No. 6,818,455 of May, et al., employs a porous carrier capillary device, sometimes referred to as a lateral flow strip, which provides mobilizable particulate labeled reagents for detection. Pregnancy test devices, well known to those of ordinary skill in the art, utilize lateral flow strips.

Prior art sampling and test devices utilizing lateral flow strips typically comprised a hollow base constructed of moisture-impervious solid material, such as plastic materials, containing a lateral flow strip that communicated indirectly with the exterior of the base through an absorbent wick which protruded from the base such that a liquid test sample could be applied to the wick and permeate therefrom to the lateral flow strip. The lateral flow strip typically included a mobile zone, containing a labeled analyte specific binding reagent, which was freely mobile within the mobile zone of the lateral flow strip when in the moist state. The lateral flow strip of the prior art further included an indicia zone, spatially distinct from the mobile zone. The indicia zone included an unlabelled specific binding reagent for the same analyte. The unlabelled specific binding reagent that was permanently immobilized on the lateral flow strip was not mobile in the moist state. The mobile zone and the indicia zone were arranged such that the liquid sample applied to the mobile zone of the lateral flow strip permeated into the indicia zone by capillary action. The presence of the analyte in the liquid sample was calorimetrically indicated in the indicia zone of the lateral flow strip as the labeled reagent permeated and become bound in the indicia zone. A user of the device observed the colorimetric results through a window in the base.

While these sampling devices were used effectively by trained users, the current devices and methods of detection were unsuitable for home diagnostic applications, because of their lack of user-friendly qualities for those not skilled in science or trained in the use of analytical devices. Further, the possibility of misplacing the multiple parts of these devices and the lack of an efficient means of distributing the devices to consumers at a low cost complicated the wide spread home use of the devices.

Further, these prior art sampling and testing devices were limited to use with liquid samples. The samples needed to be in a liquid form originally or the wick of the device needed to be separately wetted, through user manipulation, with a separately stored elution solvent, such as a liquid buffer, prior to sampling of dry surfaces of a sampling object of interest.

Accordingly, there is a need for improved methods and sampling devices for convenient use in a household for the rapid detection of proteins in specific molds, allergens, fungi, bacteria, or other protein-containing substances. More specifically, there is a need for the development of a sampling and testing device and method that are equally or superiorly reliable to the other options already available, but that are more conveniently distributable to a large number of untrained users, more conveniently usable in the home, and more easily disposed.

SUMMARY OF THE INVENTION

Disposable, simple to use sampling devices for the rapid detection of general and specific proteins, such as those of allergens, fungi, bacteria, and molds, have been developed. Embodiments of these devices allow for simple, versatile sample collection from environmental surfaces and, the sensitive and semi-quantifiable analysis of the sample for specific proteins. The device includes a base that defines a strip cavity, a wick cavity in fluid communication with the strip cavity, and a window.

Disposed within the strip cavity of the base, is a lateral flow strip having a mobile zone and an indicia zone. The window in the base overlies the indicia zone making it visible to a user of the device. The window may be covered by a transparent or translucent sheet to protect the lateral flow strip from contamination. In one embodiment, the lateral flow strip may include an absorption zone opposite the mobile zone of the lateral flow strip. The absorption zone is beyond or downstream of the indicia zone of the lateral flow strip. Thus, in this embodiment, the indicia zone is interposed between the mobile zone and the absorption zone. The absorption zone has sufficient size and porosity to receive and retain excess reagent/solvent transported beyond the indicia zone during the use of the device of the present invention.

The device further includes a sampling member slideably engageable with the wick cavity of the base. In one embodiment, the sampling member defines a solvent reservoir containing the elution solvent in a fluid-tight manner when the sampling member is fully engaged with the wick cavity of the base. The sampling member includes a handle at one end of the sampling member and a wick assembly at an opposite end of the sampling member. The wick assembly of the sampling member includes a wick holder having a member coupling end and a wick coupling end opposite the member coupling end. The member coupling end of the wick holder is slideably coupled to the sampling end of the sampling member. An absorbent wick is fixedly coupled to the wick coupling end of the wick holder.

When a user of the device of the present invention, slideably disengages and removes the sampling member from the wick cavity of the base, the elution solvent is automatically released from the solvent reservoir and flows to and is absorbed by the wick. When collecting a sample from an environmental surface of a sampling object of interest, the user of the device need not manually wet the wick with elution solvent in a separate operation. The sampling member is then used to obtain an environmental sample from a surface of a sampling object, the sample being collected with the elution solvent-wetted wick. When the sampling member is reinserted into the wick cavity of the base, the wick is thereby positively and securely placed in fluid communication with the lateral flow strip. A portion of the analyte collected from the environmental sample and now contained in the elution solvent, is transported to the indicia zone of the strip where a colorimetric analysis for the analyte is completed and the results displayed. The time required to effect the color change in the indicia zone may be used to semi-quantify the concentration of the analyte in the environmental sample when compared to the time required to effect the color change for a sample of know concentrations.

BRIEF DESCRIPTION OF THE DRAWINGS

Reference will now be made to the drawings wherein like numerals refer to like parts throughout, and wherein.

DETAILED DESCRIPTION

The embodiments disclosed herein are described in the context of a sampling and testing device for the rapid detection of specific molds, allergens, fungi, viruses, bacteria and other protein containing substances. One of ordinary skill in the art would recognize, however, that the materials and methods disclosed herein will have application in a number of other contexts where sampling and detection of the presence or absence of a particular compound is desirable, particularly where simplicity and ease of use of a sampling/detection device is important. Further, the present invention will have application in contexts where it is desirable to contain and store a fluid compound in a fluid-tight manner until a user wishes to automatically dispense the fluid to saturate an absorbent applicator wick.

Figure 1A:
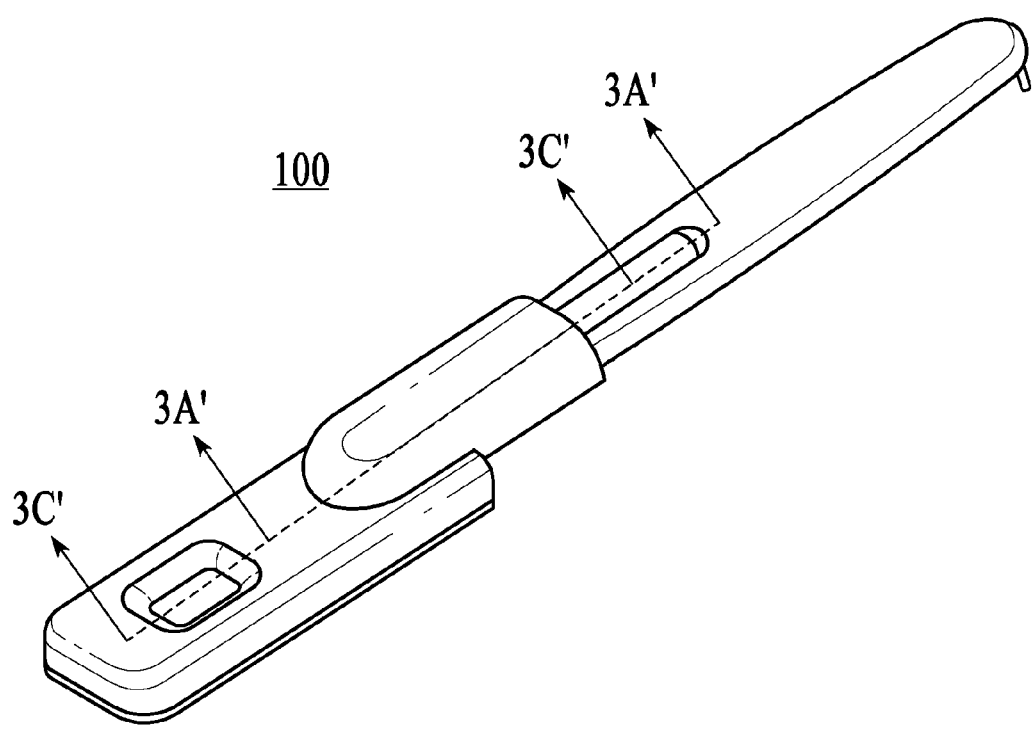
FIG. 1A is an isometric view of an embodiment of a sampling and testing device in accordance with the principles of the present invention that includes a base and a sampling member slideably engaged with base 102.
Figure 1B:
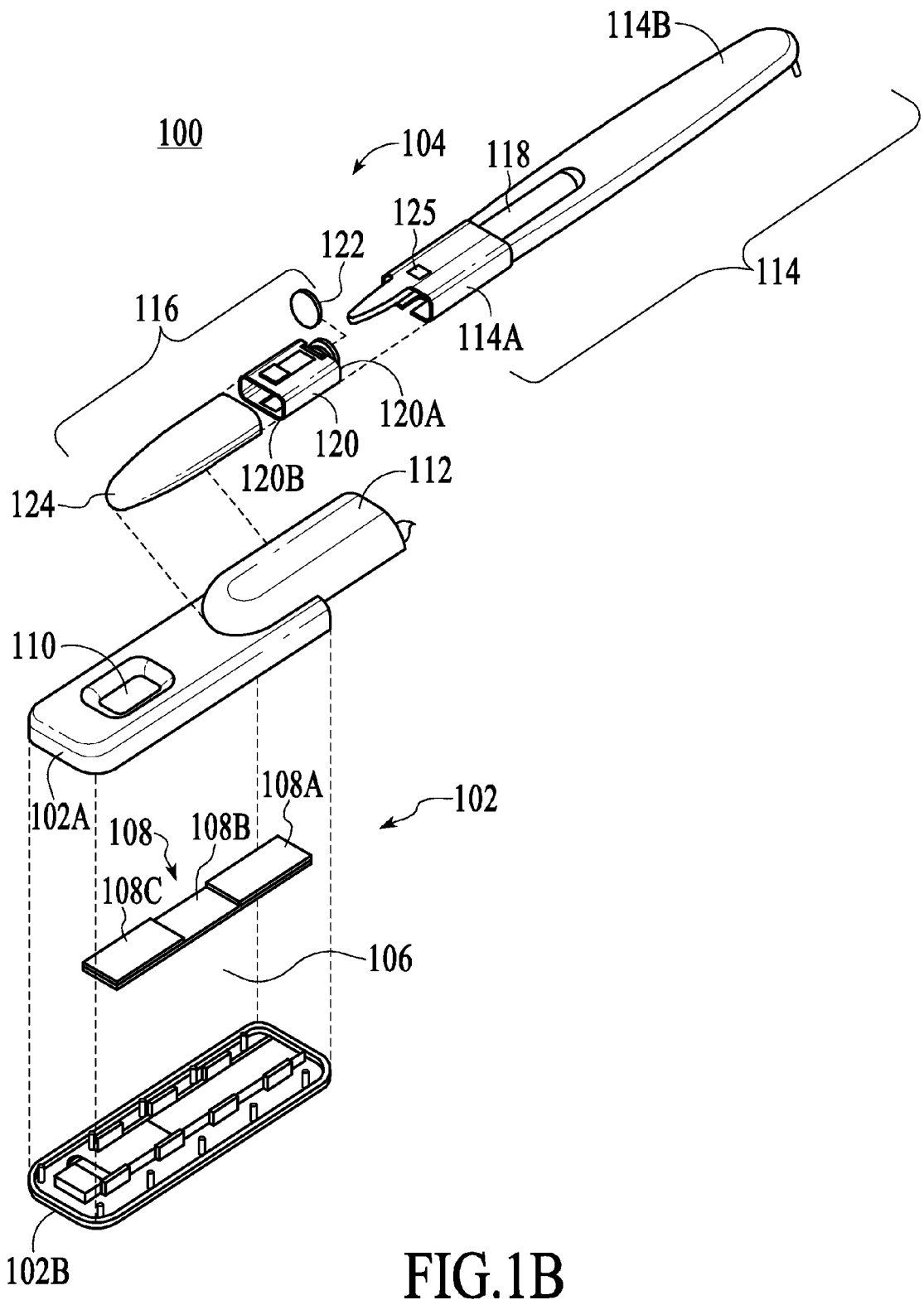
FIG. 1B is an exploded view showing further details of the sampling device of FIG. 1A.
Figure 1C:
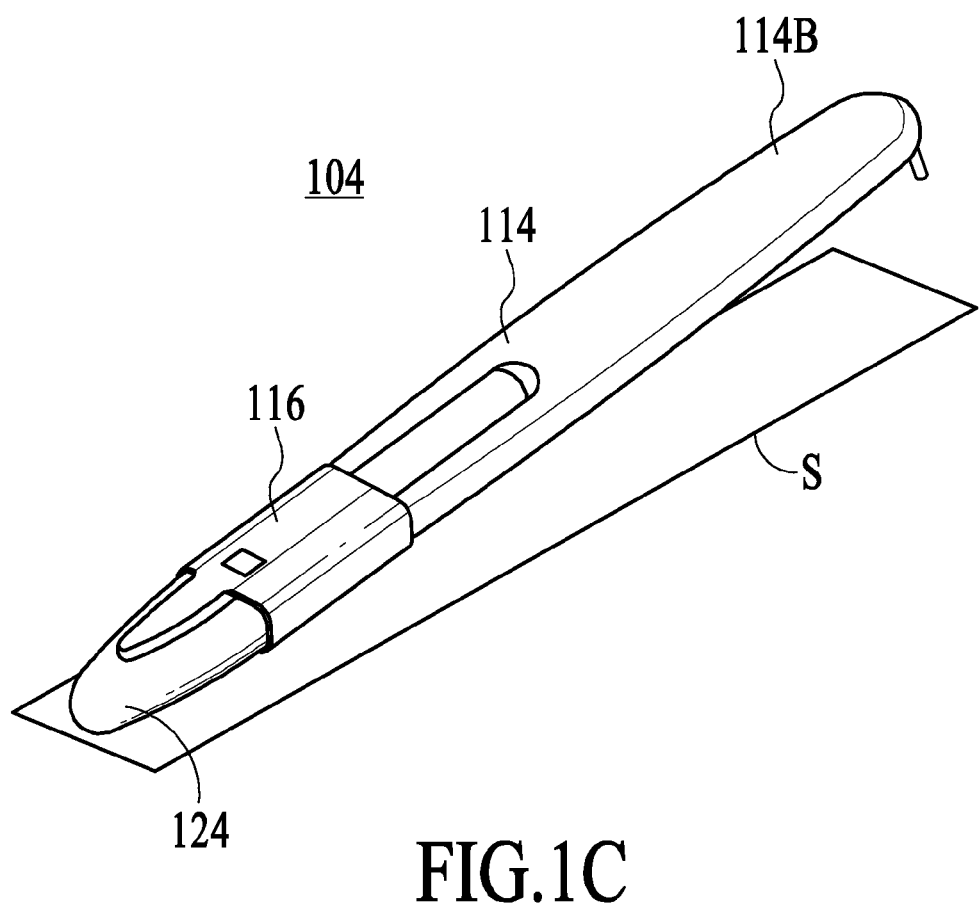
FIG. 1C is an isometric view of the device similar to FIG. 1A showing the sampling member disengaged and withdrawn from the base.

FIG. 1A is an isometric view of an embodiment of a sampling and testing device 100, hereinafter device 100, in accordance with the principles of the present invention that includes a base 102 and a sampling member 104 slideably engaged with base 102. FIG. 1B is an exploded view showing further details of the sampling device 100 of FIG. 1A. FIG. 1C is an isometric view showing sampling member 104 of device 100 slideably disengaged and withdrawn from base 102.

Referring to FIGS. 1A, 1B, and 1C together, in one embodiment, base 102 includes a base top 102A having an aperture or window 110 therethrough, and a base bottom 102B. As used herein, positional terms, such as "top" and "bottom" and the like, and directional terms, such as "up" and "down" and the like, are employed for ease of description in conjunction with the drawings. These terms are not meant to indicate that the components of the present invention must have a specific orientation except when specifically set forth below.

Base top 102A defines a wick cavity 112 adapted to receive and slideably engage sampling member 104 of device 100. Wick cavity 112 protects sampling member 104 from external contamination prior to use of device 100. Base top 102A is further adapted to couple with base bottom 102B to define a strip cavity 106 therebetween (shown in exploded view in FIG. 1B). When so formed, strip cavity 106 is in fluid communication with wick cavity 112.

A lateral flow strip 108 (FIG. 1B) is disposed within strip cavity 106 formed when base top 102A is coupled with base bottom 102B. In one embodiment, lateral flow strip 108 is configured as a substantially flat rectangular sheet of capillary material 108C, for example, nitrocellulose. At a lengthwise end of lateral flow strip 108 nearest wick cavity 112, lateral flow strip 108 includes a mobile zone 108A. Mobile zone 108A contains at least one labeled reagent capable of specific binding with an analyte of interest, such as a specific mold, fungi, or bacteria, to form a complex of the labeled reagent and the specific analyte. When in the liquid state, the labeled specific binding reagent is freely mobile within the mobile zone 108A of lateral flow strip 108. In one embodiment, the labeled reagent capable of specific binding with an analyte of interest is an antigen.

Lateral flow strip 108 further includes at least one indicia zone 108B containing a permanently immobilized and unlabelled specific binding reagent for the same analyte of interest. Indicia zone 108B is positioned at a lengthwise end of lateral flow strip 108 opposite mobile zone 108A such that a liquid sample applied to mobile zone 108A can pick up labeled specific binding reagent and thereafter permeate into indicia zone 108B through capillary material 108C. In one embodiment, the immobilized and unlabelled specific binding reagent is an antibody.

When base 102 is assembled as described, indicia zone 108B is visible through window 110 of base top 102A. The presence of the specific analyte of interest in a liquid sample is calorimetrically indicated in indicia zone 108B as the labeled reagent permeates and becomes bound in indicia zone 108B. The colorimetric results are observable by a user of device 100 through window 110. Window 110 may be covered by a transparent or translucent sheet of material (not shown) to protect and isolate indicia zone 108B from contamination from the environment external to device 100. In one embodiment, lateral flow strip further includes an absorption zone (not shown) adjacent to and downstream of indicia zone 108B. The absorption zone is adapted to receive and retain excess labeled reagent and an elution solvent 334 (FIG. 3A) that may permeate through indicia zone 108B.

As best seen in FIG. 1B, sampling member 104 includes a handle 114 having a wick coupling end 114A and a gripping end 114B opposite wick coupling end 114A. Handle 114 defines a solvent reservoir 118 adapted to contain an elution solvent 334 (FIG. 3A). In one embodiment, elution solvent 334 is a liquid buffer comprising phosphate buffers or alcohol based buffers. Solvent reservoir 118 is configured as a hollow, open-ended cylinder having a reservoir opening 118A on one end. Handle 114 further defines a withdrawal indent 125. As described and illustrated more fully below with reference to FIGS. 3A and 3B, withdrawal indent 125 is adapted to cooperate with a withdrawal snap detent 232 (FIGS. 2B, 3A and 3B) during the slideable withdrawal of sampling member 104 from base 102 by a user of device 100.

Sampling member 104 further includes a wick assembly 116 coupled to handle 114. Wick assembly 116 of sampling member 104 includes a wick holder 120 having a handle coupling end 120A and a wick coupling end 120B opposite handle coupling end 120A. Handle coupling end 120A of wick holder 120 is adapted to initially slideably couple with wick coupling end 114A of handle 114. Thus, as described and illustrated more fully below with reference to FIG. 3A, handle 114 may slideably move outwardly away from wick holder 120 when a user of device 100 initiates withdrawal of sampling member 104 from base 102.

A wick 124 is fixedly coupled to and secured to wick holder 120 at wick coupling end 120B of wick holder 120. In one embodiment, wick 124 is formed from an absorbent material, such as by way of example and not limitation, synthetic polyurethane, polyester, and polyproplene. Wick 124 is adapted to receive, distribute, and retain a fluid. A seal crush rib (not shown), well known to those of ordinary skill in the art, may be placed around the perimeter of wick holder 120 adjacent handle coupling end 120A of wick holder 120 to prevent fluid from bypassing wick 124. As described and illustrated more fully below with reference to FIGS. 3A and 3B, a sealing ring 122 assists in formation of a releasable fluid-tight seal between solvent reservoir 118 and wick holder 120.

Figure 2A:
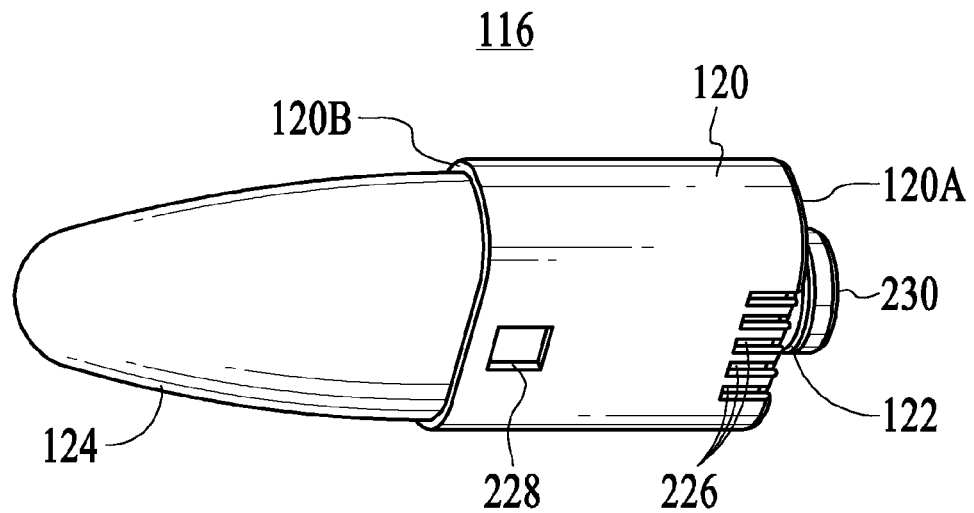
FIG. 2A is a top close-up view of a wick assembly of FIG. 1B that includes a wick holder and a wick fixedly coupled to the wick holder.

FIG. 2A is a top close-up view of wick assembly 116 of FIG. 1B with wick 124 fixedly coupled to wick coupling end 120B of wick holder 120. As shown, wick holder 120 includes one or more slots 226. Slots 226 are configured as openings through wick holder 120 about at least a portion of wick holder 120 at its handle coupling end 120A. Slots 226 provide passageways that place the exterior of wick holder 120 in fluid communication with wick 124. Fluid may pass through slots 226 from the exterior of wick holder 120 to saturate wick 124. As would be apparent to one of ordinary skill in the art, other configurations and positions for slots 226 to provide fluid communication to wick 124 are possible.

As also shown in FIG. 2A, wick holder 120 further includes a catch indent 228. As described and illustrated more fully below with reference to FIGS. 3A and 3B, catch indent 228 is adapted to cooperate with a catch detent 336 (FIGS. 3A and 3B) in locking engagement during the slideable withdrawal of sampling member 104 from base 102 (FIG. 1C) by a user of device 100. Finally as shown, wick holder 120 includes a reservoir plug 230. As also described and illustrated more fully below with reference to FIGS. 3A and 3B, reservoir plug 230 is adapted to cooperate with reservoir 118, and more specifically with reservoir opening 118A, (FIG. 1B) in sealing engagement to form a fluid-tight seal therebetween. In the embodiment shown, reservoir plug 230 is configured as a cylindrical stopper or bung fixedly coupled to or integral with wick holder 120 at its handle coupling end 120A. In one embodiment, sealing ring 122, configured as an "O" ring, well known to those of ordinary skill in the art, circumscribes reservoir plug 230 to aid in the formation of the fluid-tight seal between reservoir plug 230 and reservoir opening 118A.

Figure 2B:
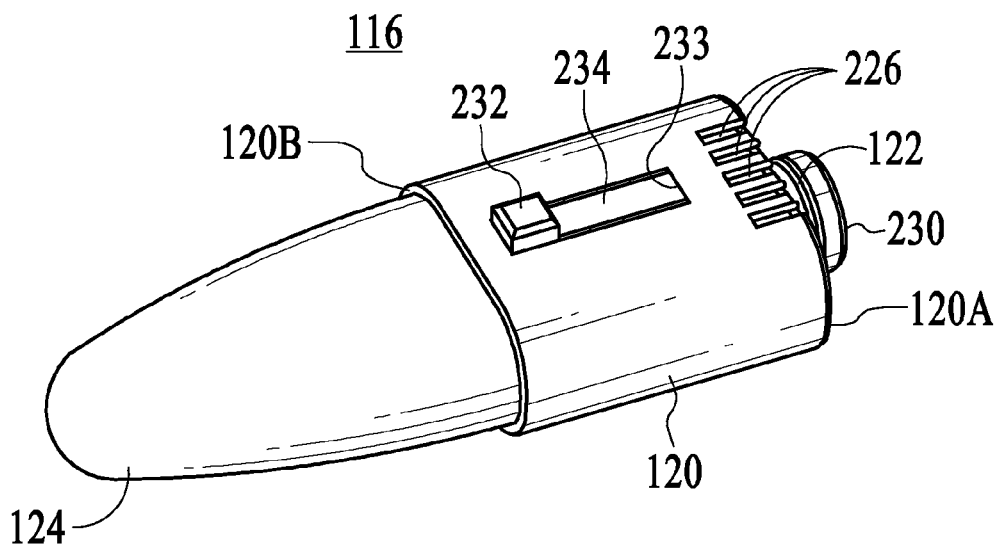
FIG. 2B is a bottom close-up view of the wick assembly of FIG. 1B.
Figure 3A:
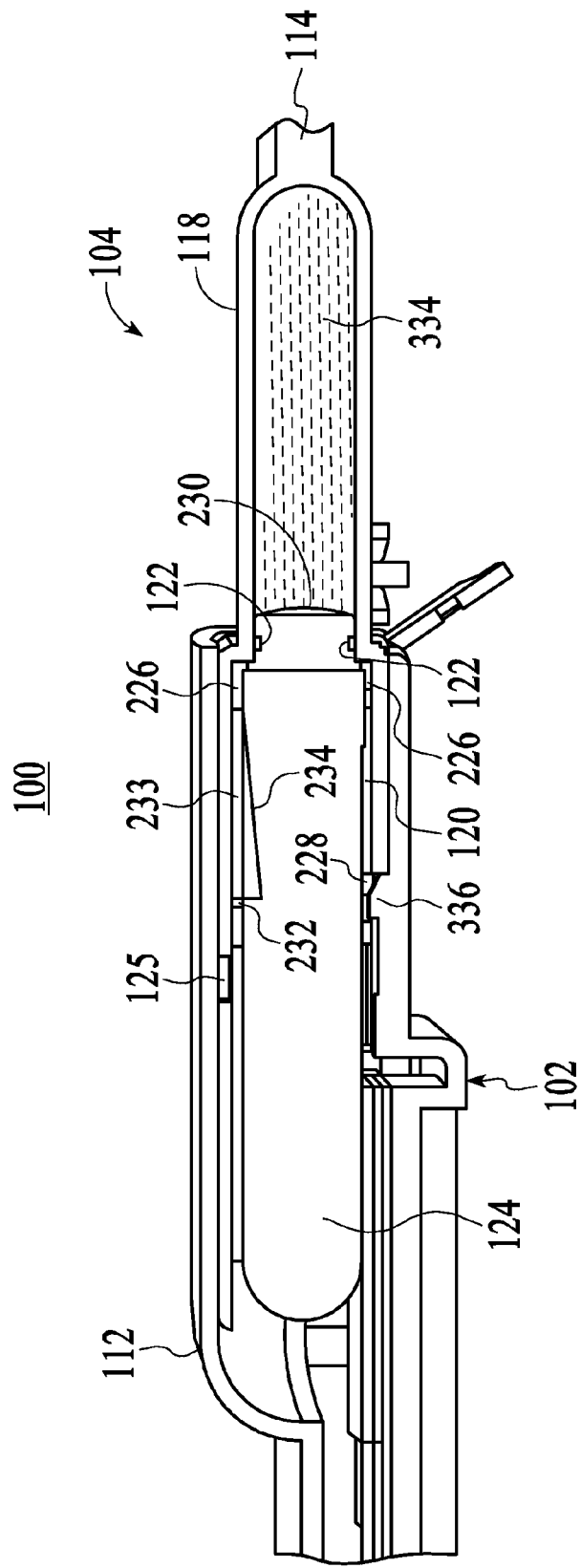
FIG. 3A is a partial cross-section side view of the device taken along the line 3A'-3A' of FIG. 1A.

FIG. 2B is a bottom close-up view of wick assembly 116 of FIG. 1B with wick 124 fixedly coupled to and partially retained within wick holder 120. Wick holder 120 includes a withdrawal snap detent 232 coupled to a flex member 234 at one end thereof. Flex member 234 is coupled to the top of wick holder 120 only at the end of flex member 234 opposite withdrawal snap detent 232, thereby forming a living hinge 233 at the point of coupling. Withdrawal snap detent 232 may pivot about living hinge 233 inwardly toward the inside of wick holder 120. Wick 124, partially contained within wick holder 120, may be formed from crushable or flexible material to avoid interference with and to accommodate the inward movement of withdrawal snap detent 232. When so pivoted inwardly, flex member 234 produces an elastic biasing force tending to return withdrawal snap detent 232 to its relaxed position before pivoting. As described and illustrated more fully directly below with reference to FIGS. 3A and 3B, withdrawal snap detent 232 is adapted to cooperate with withdrawal indent 125 (FIG. 1B) in temporary locking engagement during the initial slideable withdrawal of sampling member 104 from base 102 by a user of device 100.

FIG. 3A is a partial cross-section side view of device 100 taken along the line 3A'-3A' of FIG. 1A. As in FIG. 1A, sampling member 104 is fully engaged with base 102 of device 100. In this configuration, wick assembly 116 (FIG. 1A) is enclosed within wick cavity 112 of base 102. When engaged as shown, solvent reservoir 118 retains an elution solvent 334, which, in one embodiment, is a flow able fluid. The cylindrically shaped outer peripheral sidewall of reservoir plug 230 abuts and sealingly engages the cylindrically shaped inner sidewall of solvent reservoir 118 to seal off the opened end of solvent reservoir 118 to contain elution solvent 334 within reservoir 118.

Further, in this fully engaged configuration, catch indent 228 of wick holder 120 is lockingly engaged with a catch detent 336 of base 102 by interference therebetween. The protrusion of catch detent 336 is within the indentation of catch indent 228. In this configuration, catch indent 228 and catch detent 336 cooperate to resist both inward and outward sliding motion of wick holder 120, and consequently wick 124 coupled thereto, relative to base 102. Still further, in this fully engaged configuration, withdrawal snap detent 232 is flexed inwardly toward the inside of wick holder 120. As described above with reference to FIG. 2B, withdrawal snap detent 232 may pivot inwardly toward the inside of wick holder 120 about living hinge 233. When so pivoted inwardly as shown, flex member 234 produces an elastic biasing force tending to return withdrawal snap detent 232 outwardly toward its relaxed position before pivoting. However, as shown in FIG. 3A, this biasing force is resisted by the top of handle 114. More particularly, the biasing force tending to return snap detent 232 outwardly toward its relaxed position is resisted by the top of wick coupling end 114A that is beyond withdrawal indent 125 in a direction toward reservoir 118. Thus, in this fully engaged configuration, snap detent 232 is contained within the inside of wick holder 120, while, at the same time, an outwardly biasing force on snap detent 232 is produced by flex member 234.

Figure 3B:
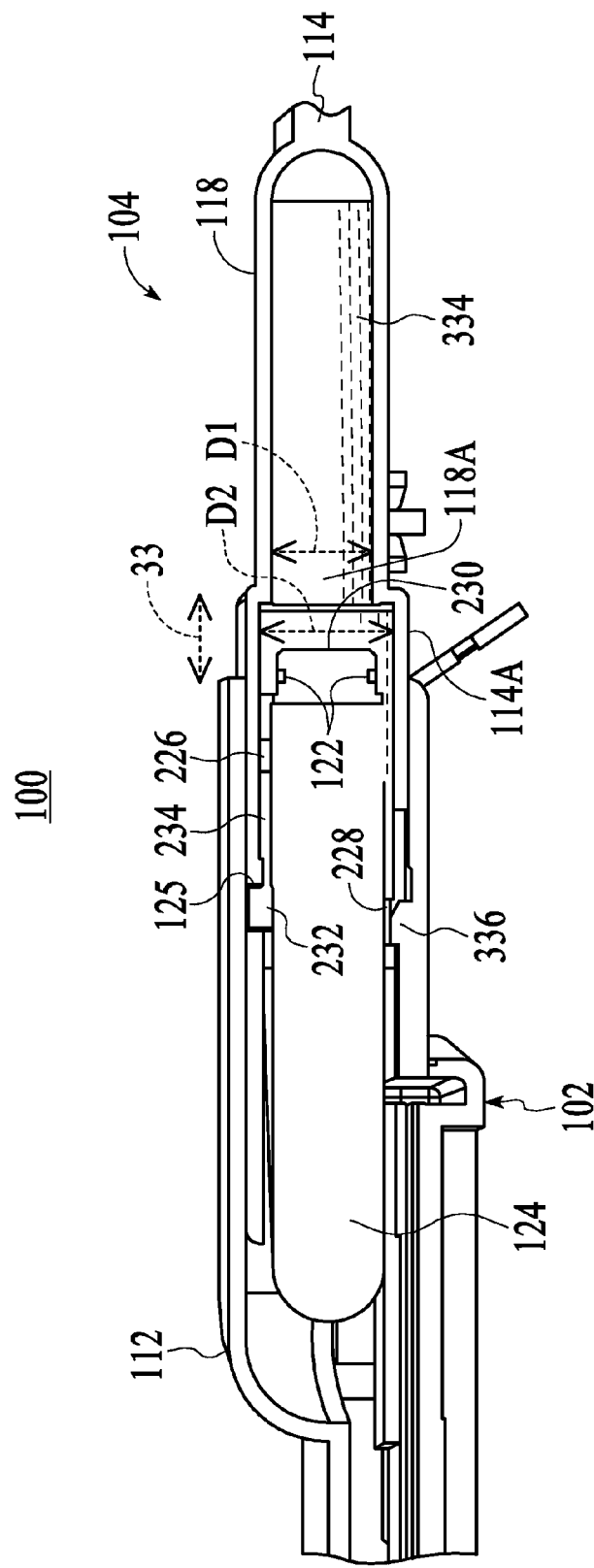
FIG. 3B is a partial cross-section side view of the device of FIG. 1A, similar to FIG. 3A but with the sampling member partially withdrawn from the base.

FIG. 3B is a partial cross-section side view of device 100 of FIG. 1A, similar to FIG. 3A but with sampling member 104 partially withdrawn from base 102. As shown by dimension arrow 335, handle 114 has moved outwardly relative to wick holder 120. This outward movement may be initiated by a user of device 100. A user may grasp and pull outwardly on gripping end 114B of handle 114 (FIG. 1B) with one hand while, at the same time, holding base 102 stationary with the other hand. Since catch indent 228 of wick holder 120 is lockingly engaged with catch detent 336 of base 102, as described above with reference to FIG. 3A, wick holder 120 is initially constrained from moving outwardly as handle 114 of sampling member 104 is withdrawn from base 102.

Recalling that handle coupling end 120A of wick holder 120 is adapted to slideably engage with wick coupling end 114A of handle 114, handle 114 may slideably move outwardly away from wick holder 120. As sampling member 104 is withdrawn from a stationary base 102, wick holder 120 is held stationary to base 102 by the cooperation of catch indent 228 and catch detent 125 as described, and handle coupling end 120A of wick holder 120 slides within wick coupling end 114A of handle 114.

In this manner, reservoir plug 230 is released from sealing engagement with reservoir 118. At the point of partial withdrawal shown, because of the outward movement of handle 114 relative to wick holder 120, reservoir plug 230 of wick holder 120 clears reservoir opening 118A of reservoir 118 and enters a wide portion of handle 114 at its wick coupling end 114A. Reservoir opening 118A has a first diameter D1 and wick coupling end 114A of handle 114 has a second diameter. First diameter D1 of reservoir opening 118A is smaller than second diameter D2 of wick coupling end 114A of handle 114. Further, as shown, sealing ring 122 circumscribing reservoir plug 230 has likewise cleared reservoir opening 118A of reservoir 118.

Thus at this point of partial slideable withdrawal of sampling member 104 from base 102, elution solvent 334 flows from reservoir 118 into wick coupling end 114A of handle 114 through the gap created between reservoir plug 230 and reservoir opening 118A by the partial withdrawal of sampling member 104 from base 102. As regent 334 flows into wick coupling end 114A of handle 114, strainer slots 226 (see also FIGS. 2A and 2B), configured as openings through wick holder 120, provide passageways for elution solvent 334 to flow through and contact wick 124. Since, as noted, wick 124 is formed from absorbent material, elution solvent 334 is received, distributed, and retained on wick 124.

Further, at the point of partial withdrawal of sampling member 104 from base 102 shown in FIG. 3B, withdrawal snap detent 232 of handle 114 lockingly engages withdrawal indent 125 of wick coupling end of wick holder 120. As described above with reference to FIG. 2B, wick holder 120 includes withdrawal snap detent 232 coupled to flex member 234 at one end thereof. As described above with reference to FIG. 3A, an outwardly directed biasing force on withdrawal snap detent 232 is produced by flex member 234 when sampling member 104 is fully inserted within base 102.

When withdrawal snap detent 232 aligns with withdrawal indent 125, the biasing force on withdrawal snap detent 232 operates to move withdrawal snap detent 232 outwardly toward its relaxed position there to form a locking engagement with withdrawal indent 125. The initial outward movement of handle 114 relative to wick holder 120 provides for alignment of withdrawal snap detent 232 with withdrawal indent 125. In one embodiment, withdrawal snap detent 232 produces a "snapping" sound as it lockingly engages withdrawal indent 125 during partial withdrawal of sampling member 104 from base 102 by a user of device 100.

As a user of device 100 attempts further withdrawal of sampling member 104 from base 102 beyond that show in FIG. 3B a conflict occurs. The locking engagement of catch indent 228 with catch detent 336 restrains the outward movement of wick holder 120. At the same time, the locking engagement of withdrawal snap detent 232 and withdrawal indent 125 transfers the withdrawal force supplied by a user to handle 114 of sampling member 104 to wick holder 120 of sampling member 104, thereby motivating wick hold 120 to move outwardly from base 102 along with handle 114.

In accordance with the principle of the present invention, the locking engagement of catch indent 228 with catch detent 336 is less forceful than the locking engagement of withdrawal snap detent 232 with withdrawal indent 125. Thus, as a user continues to withdraw sampling member 104 from base 102, the locking engagement of catch indent 228 of wick holder 120 with catch detent 336 of base 102 preferentially yields over the locking engagement of withdrawal snap detent 232 and withdrawal indent 125. Thus wick hold 120, still lockingly engaged with and coupled to handle 114, is withdrawn along with handle 114.

The preferential yielding of the locking engagement of catch indent 228 with catch detent 336 may be accomplished variously. In one embodiment, for example, the spatial interference between catch indent 228 of wick holder 120 and catch detent 336 is less than the spatial interference between withdrawal snap detent 232 and withdrawal indent 125. In another embodiment, catch detent 336 shears from base 102 as withdrawal of sampling member 104 from base 102 proceeds. In still another embodiment, catch indent 228 and/or catch detent 336 deform and yield during continued withdrawal to release the locking engagement of catch indent 228 with catch detent 336. Other embodiments that provide for preferential yielding of the locking engagement of catch indent 228 of wick holder 120 with catch detent 336 of base 102 would be apparent to those of ordinary skill in the art.

Referring again to FIG. 1C, once sampling member 104, including handle 114 and wick assembly 116 having wick 124 saturated with elution solvent 334 (not shown in FIG. 1C), is fully withdrawn from base 102 (FIG. 1B), a user of device 100 contacts and wipes an environmental surface S of a sampling object with wick 124 to collect a sample of materials contained on environmental surface S. Since wick 124 has been wetted with elution solvent 334 (FIG. 3B) at withdrawal of sampling member 104 from base 102 as described above with reference to FIGS. 3A and 3B, there is no need for the user of device 100 to manually wet wick 124 in a separate operation. A user simply manipulates sampling member 104 with by grasping handle 114 at its gripping end 114B to collect a sample with wick 124 wetted with elution solvent 334. Environmental surface S may contain allergens, viruses, bacteria and other protein containing analytes of interest, which are collected for analysis.

Figure 3C:
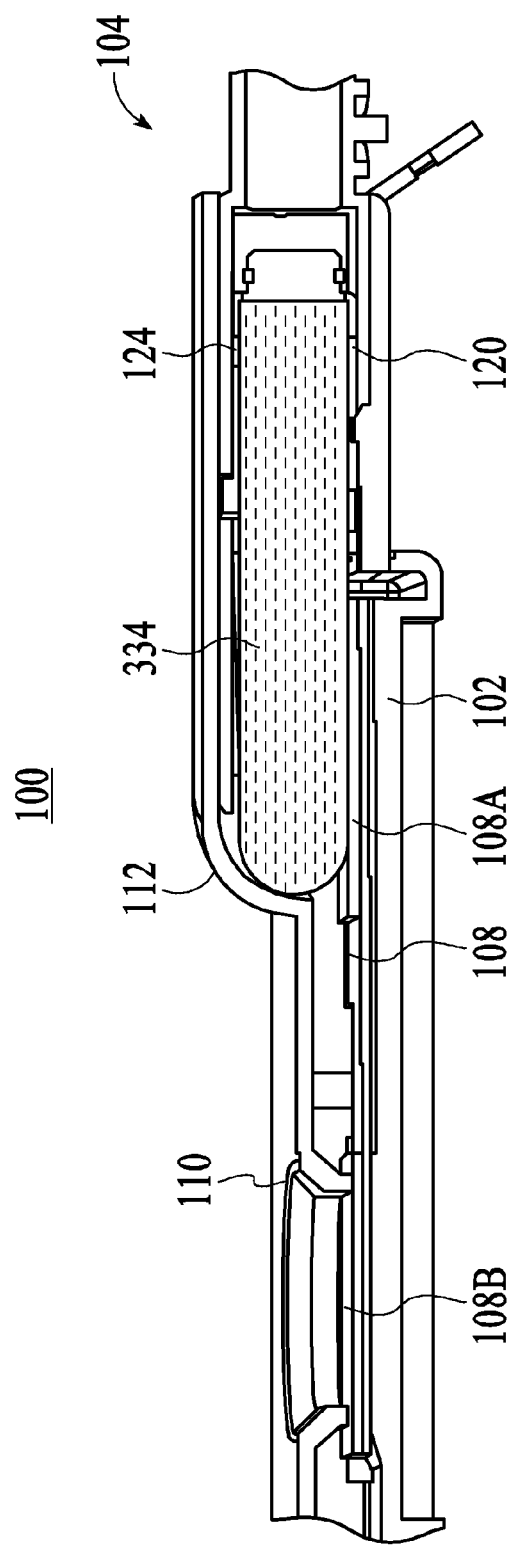
FIG. 3C is a partial cross-section side view of the device of FIG. 1A, taken along line 3C'-3C' with the sampling member reinserted into the base 102 after a sample has been collected from environmental surface S of a sampling object.

After a sample of material contained on environmental surface S is collected, a user slideably reinserts sampling member 104 back into base 102. FIG. 3C is a partial cross-section side view of device 100 of FIG. 1A, taken along line 3C'-3C' with sampling member 104 reinserted into base 102 after a sample has been collected from environmental surface S (FIG. 1C) of a sampling object. As noted above with reference to FIG. 3B, during withdrawal of sampling member 104 from base 102, handle 114 (FIG. 3B) has moved outwardly relative to wick holder 120, when compared to the position of handle 114 to wick holder 120 before withdrawal (FIG. 3A). Thus, during withdrawal, the overall length of sampling member 104, from wick 124 to gripping end 114B of handle 114 (FIG. 3C), increases by the amount shown by dimension arrow 335 (FIG. 3B). As lengthened sampling member 104 is reinserted into base 102, wick 124, now fixedly coupled to wick holder 120, encounters the end of wick cavity 112 (see also FIG. 1B) and bends downwardly to securely and positively compress against lateral flow strip 108. In this manner, the sample of materials contained on environmental surface S, which were collected within regent 334 absorbed on wick 124 during sampling, are placed in fluid communication with and transferred to mobile zone 108A of lateral flow strip 108. Lateral flow strip provides a calorimetric indication of specific allergens, molds, viruses, bacteria, fungi, and other protein containing substances of interest that the environmental surface S may contain at indicia zone 108B of lateral flow strip 108 through window 110 of base 102.

Thus, embodiments of the present invention provide a sampling and test device that includes a sampling member slideable coupled to base that contains a lateral flow strip adapted to detect specific molds, allergens, viruses, fungi, bacteria, and other protein containing substances. The sample member defines a solvent reservoir that stores a reagent before the device is used to sample and test environmental surfaces. During withdrawal by a user of the sampling member from the base, the elution solvent stored in the reservoir is automatically released to a wick assembly of the sampling member. The wick assembly includes a wick adapted to receive, distribute, and retain the elution solvent. The user of the device need not manually wet the wick with elution solvent in a separate operation. After a user samples an environmental surface with the elution solvent wetted wick of the withdrawn sampling member, the sampling member is slideable reinserted into the base where the wick contacts the lateral flow strip contained in the base. The wick transfer at least a portion of sample and the elution solvent to the lateral flow strip for the colorimetric detection of specific molds, allergens, viruses, bacteria, fungi, and other protein containing substances that may be contained in the sample. The colorimetric results of the test are displayed through a window in the base.

The present invention has been described herein in considerable detail to provide those skilled in the art with information relevant to apply the novel principles and to construct and use such specialized components as are required. Specifically, embodiments of the sampling device and method have been described with reference to the detection of protein-containing substance such as mold, bacteria, fungi, and allergens. More specifically, the present invention has been described with reference to a colorimeter test. However, those of ordinary skill in the art will readily appreciate that the present invention is adaptable to any number of colorimetric tests. Further, it is to be understood that the present invention can be carried out by different equipment, materials and devices, and that various modifications, both as to the equipment and operating procedures, can be accomplished without departing from the scope of the invention itself.

For example, the solvent reservoir of the present invention may be divided by a separating baffle into two or more compartments. In this embodiment, when withdrawing the sampling member from the base only one fluid is released from its separate compartment to be absorbed on the wick of the sampling member, with the second fluid being retained within its separate reservoir compartment by a septum or the like. Upon reinsertion of the sampling member into the base after a sample has been obtained, the septum retaining the second fluid may be punctured with, for example, a manually operated prod, to release the second fluid.

This embodiment would find application where the environmental surface contains only a low concentration of the specific analyte below the level of detection of the lateral flow strip. In this example, the first fluid, released and absorbed by the wick upon withdrawal of the sampling member, could be a growth medium for the analyte of interest. The reinsertion of the sampling member could be delayed for a period of time necessary for the analyte to propagate in the growth medium to a detectable concentration. Upon delayed reinsertion of the sampling member, the second fluid, such as an elution solvent for the completion of the lateral flow strip analysis, could then be manually released to initiate testing.

In another example involving a dual chambered reservoir, specific antibiotics or biocides could be released to the wick from a first reservoir chamber when the sampling member is withdrawn form the base. Thus, only analytes that is resistance to the specific antibiotic will be tested. These examples could be combined by adding selective biocide or antibiotic agents in a growth medium applied to the wick upon withdrawal of the sampling member from the base.

In another embodiment, a dispensing device according to the present invention could be used as a dispenser for fluid cosmetics, externally applied fluid medicines and the like. The fluid compound is stored and then automatically released from a fluid compound reservoir in a dispensing applicator to a wick upon withdrawal of the dispensing applicator from a base. Other details of the dispenser are similar to those described above for the sampling and testing device and so are not repeated here. The wick could then by used as an applicator for the absorbed cosmetic or medicine. In this embodiment, a lateral flow strip, strip cavity, and window would not be required since no analysis is performed.

In yet another example, a general method for the rapid detection of specific molds, allergens, viruses, fungi, bacteria, and other protein containing substances includes: providing a sampling and testing device for collecting a sample and detecting one or more specific protein containing analytes of interest; removing a wick assembly having a wick from a base of the sampling and testing device; optionally, releasing to the wick one or more fluids stored separately in one or more reservoirs of the sampling and testing device; collecting a sample on the wick of the wick assembly; reinserting the wick assembly into the base after obtaining a sample; optionally releasing to the wick one or more additional fluids stored separately in the one or more reservoirs, and; observing calorimetric results displayed on an indicia zone of a lateral flow strip contained within the sampling and testing device.

The method can be adapted to detecting specific molds, allergens, viruses, fungi, bacteria, and other protein containing substances in environmental samples or in biological samples such as human spittle or nasal fluid. In one embodiment, the fluid is an elution solvent that is released when the wick assembly is first removed from the base. In another embodiment, the fluid is a growth medium for an analyte of interest. In yet another embodiment, no fluid is released to the wick upon withdrawal of the wick assembly from the base. In this embodiment, a fluid is released to the wick upon reinsertion of the wick assembly into the base after sampling.

We claim:

1. A sampling and testing device for collecting an environmental sample and detecting an analyte of interest suspected of being present in said environmental sample, said sampling and testing device comprising:
    a base, said base defining a strip cavity, a wick cavity, and a window;
    a lateral flow strip disposed within said strip cavity of said base, said lateral flow strip having a mobile zone and an indicia zone adjacent said mobile zone;
    a sampling member having a handle and a wick assembly coupled to said handle, wherein said sampling member defines a solvent reservoir containing an elution solvent;
    wherein said wick assembly comprises:
        a wick holder having slots therethrough; and
        a wick coupled to said wick holder;
    wherein said wick assembly is slideably engageable with said wick cavity of said base;
    wherein said elution solvent is initially contained within said solvent reservoir in a fluid-tight manner when said sampling member is fully engaged with said base; and
    wherein said elution solvent is released from said solvent reservoir into said wick through said slots of said wick holder when said sampling member is withdrawn from said base.

2. The sampling and testing device of claim 1 wherein said indicia zone is visible through said window.

3. The sampling and testing device of claim 1 wherein the presence of a specific analyte of interest in a sample is indicated in said indicia zone by colorimetric display.

4. The sampling and testing device of claim 1 wherein said elution solvent comprises a buffer solution.

5. The sampling and testing device of claim 4 wherein said buffer solution is selected from the group consisting of phosphate buffers and alcohol based buffers.

6. The sampling and testing device of claim 1 wherein said lateral flow strip further comprises an absorption zone downstream of said indicia zone of said lateral flow strip.

7. The sampling and testing device of claim 6 wherein said absorption zone has sufficient size and porosity to receive and retain said elution solvent that permeates beyond said indicia zone during use of said sampling and testing device.

8. The sampling and testing device of claim 1 wherein said lateral flow strip is configured as a substantially flat rectangular sheet of capillary material.

9. The sampling and testing device of claim 8 wherein said capillary material comprises nitrocellulose.

10. The sampling and testing device of claim 1 wherein said mobile zone contains at least one labeled reagent capable of specific binding with an analyte of interest.

11. The sampling and testing device of claim 10 wherein said analyte of interest is selected from the group consisting of allergens, viruses, bacteria, and other protein containing substances.

12. The sampling and testing device of claim 11 wherein said indicia zone contains a permanently immobilized and unlabelled specific binding reagent for said analyte of interest.

13. The sampling and testing device of claim 1 wherein said solvent reservoir is configured as a hollow cylinder having a reservoir opening on one end of said solvent reservoir.

14. The sampling and testing device of claim 1 wherein said a wick holder further comprises a reservoir plug coupled to said wick holder and adapted to cooperate with said reservoir in sealing engagement to form a fluid-tight seal therebetween.

15. The sampling and testing device of claim 14 wherein said reservoir plug includes a sealing ring circumscribing said reservoir plug.

* * * * *